(12) United States Patent
Mikolajczyk et al.

(10) Patent No.: US 6,423,503 B1
(45) Date of Patent: *Jul. 23, 2002

(54) FORMS OF FREE PROSTATE-SPECIFIC ANTIGEN (PSA) AND THEIR ASSOCIATION WITH PROSTATE TISSUES FROM PROSTATE PERIPHERAL ZONE AND TRANSITION ZONE

(75) Inventors: Stephen D. Mikolajczyk, San Diego; Tang Jang Wang, Poway; Harry G. Rittenhouse, Del Mar; Robert L. Wolfert, San Diego, all of CA (US); Kevin Slawin, Houston, TX (US)

(73) Assignees: Hybritech Incorporated, Fullerton, CA (US); Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/303,339

(22) Filed: Apr. 30, 1999

(51) Int. Cl.[7] .................. G01N 33/574; G01N 33/53; G01N 33/48; A61K 49/00; C12Q 1/00
(52) U.S. Cl. ................ 435/7.23; 435/4; 435/7.1; 435/7.2; 435/960; 435/975; 436/63; 436/64; 436/811; 436/813; 424/9.1
(58) Field of Search ............... 435/4, 7.1, 7.2, 435/7.23, 960, 975; 436/63, 64, 811, 813; 424/9.1

(56) References Cited

U.S. PATENT DOCUMENTS 5,501,983 A * 3/1996 Lilja et al.
5,858,685 A    1/1999 Stamey et al.
6,300,088 B1 * 10/2001 Enghild et al.

OTHER PUBLICATIONS

Christensson, Anders et al., "Enzymatic activity of prostate–specific antigen and its reactions with Extracellular serine proteinase inhibitors", Eur. J. Biochem. 194, 755–763, (1990).

Watt, Kenneth, "Human prostate–specific antigen: Structural and functional similarity with serine Proteases", Proc. Natl. Acad. Sci. USA, vol. 83, pp. 3166–3170 May 1986.

Chen, Zuxiong, et al., "Prostate Specific Antigen In Benign Prostatic Hyperplasia: Purification And Characterization", The Journ. Of Urology, vol. 157, 2166–2170, Jun. 1997.

Chu, Larry F., et al., "Different Molecular Forms Of Uncomplexed Prostate Specific Antigen (PSA) Show Similar Immunoreactivities", The Journ. Of Urology, vol. 161, 2009–2012, Jun., 1999.

Hilz, Helmuth et al., "Molecular Heterogeneity of Free PSA in Sera of Patients with Benign and Malignant Prostate Tumors", Eur. Urol. 1999; 36:286–292.

* cited by examiner

Primary Examiner—Anthony C. Caputa
Assistant Examiner—Gary B. Nickol
(74) Attorney, Agent, or Firm—William H. May; D. David Hill; Hogan & Hartson, LLP

(57) ABSTRACT

A method of distinguishing prostate cancer from benign prostatic hyperplasia (BPH) is provided. The mathematical combination or ratio of proPSA and BPSA serum or tissue markers may be used for distinguishing benign prostatic hyperplasia (BPH) from prostate cancer. It is the discovery of the present invention that BPSA is preferentially elevated in transition zone prostate tissue whereas pPSA is elevated in the peripheral zone of prostate tissue. A kit for aiding in distinguishing BPH from prostate cancer is also provided.

38 Claims, 6 Drawing Sheets

PSA Sequence

1 ↓

| IVGGWECEKH | SQPWQVLVAS | RGRAVCGGVL | VHPQWVLTAA | 40 |
| HCIRNKSVIL | LGRHSLFHPE | DTGQVFQVSH | SFPHPLYDMS | 80 |
| LLKNRFLRPG | DDSSHDLMLL | RLSEPAELTD | AVKVMDLPTQ | 120 |

145 ↓

| EPALGTTCYA | SGWGSIEPEE | FLTPKKLQCV | DLHVISNDVC | 160 |

182 ↓

| AQVHPQKVTK | FMLCAGRWTG | GKSTCSGDSG | GPLVCNGVLQ | 200 |
| GITSWGSEPC | ALPERPSLYT | KVVHYRKWIK | DTIVANP | 237 |

Figure 6

SEQUENCE LISTING

<160> NUMBER OF SEQ ID NOS: 2

<210> SEQ ID NO 1
<211> LENGTH: 7
<212> TYPE: PRT
<213> ORGANISM: Homo sapiens

<400> SEQUENCE: 1

```
Ala Pro Leu Ile Leu Ser Arg
1               5
```

<210> SEQ ID NO 2
<211> LENGTH: 237
<212> TYPE: PRT
<213> ORGANISM: Homo sapiens

<400> SEQUENCE: 2

```
Ile Val Gly Gly Trp Glu Cys Glu Lys His Ser Gln Pro Trp Gln Val
1               5                   10                  15

Leu Val Ala Ser Arg Gly Arg Ala Val Cys Gly Val Leu Val His
            20                  25                  30

Pro Gln Trp Val Leu Thr Ala Ala His Cys Ile Arg Asn Lys Ser Val
            35                  40                  45

Ile Leu Leu Gly Arg His Ser Leu Phe His Pro Glu Asp Thr Gly Gln
        50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

FORMS OF FREE PROSTATE-SPECIFIC ANTIGEN (PSA) AND THEIR ASSOCIATION WITH PROSTATE TISSUES FROM PROSTATE PERIPHERAL ZONE AND TRANSITION ZONE

BACKGROUND OF THE INVENTION

1. Field of the Invention

The invention relates generally to prostate-specific antigen (PSA) and specifically to different forms of PSA and their association with prostate cancer and benign prostate disease.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

The measurement of serum PSA is a widely used marker for the early detection of human prostate cancer (1–3). Elevated levels of PSA in the blood are symptomatic of prostate disease, which is primarily manifested as either benign prostate hyperplasia (BPH) or prostate cancer (PCa). However, in the range 4–10 ng PSA per ml of serum it is difficult to distinguish BPH from PCa without additional tests such as digital rectal exam and prostate needle biopsy.

Recently, it has been demonstrated that the level of free or non-complexed PSA in serum can improve the discrimination of PCa from BPH (4–6). An elevated ratio of free PSA to total PSA is more highly correlated with BPH. The reasons for the presence of free PSA in serum has therefore become the subject of intensive investigation.

It is generally accepted that the free PSA in serum is enzymatically inactive. PSA is a serine protease capable of complex formation with serum protease inhibitors. Human serum contains high levels of $\alpha_1$antichymotrypsin (ACT) and $\alpha_2$macroglobulin, both of which have been shown to complex with PSA (7). The majority of PSA in serum that can be detected by immunoassay is in a complex with ACT (4; 6). From 70–95% of the PSA in serum is in a complex with ACT. Studies with PSA purified from seminal plasma have shown that about 30% of the PSA does not form a complex with ACT. This fraction of PSA contains an internal peptide bond cleavage at Lys145 which renders it inactive (4; 6; 7). A more detailed characterization of the inactive forms of PSA from seminal plasma revealed PSA clipped at both Lys145 and Arg85, in addition to a fraction of PSA which was not clipped but which did not form a complex with ACT (8).

The analysis of PSA from sources other than seminal plasma has been more limited. PSA was isolated from BPH nodules (9), where it was found to contain more enzymatically inactive PSA than seminal plasma PSA and to contain additional new clips after Ile1, His54, Phe57 and Lys146. The proenzyme form of PSA (pPSA) has also been reported in the serum of PCa patients (10). Both clipped and proenzyme forms of PSA could therefore be components in the serum of patients with prostate disease.

However, no one has studied the source of variable forms of PSA in serum. The association of both the clipped and proenzyme forms of PSA with different prostate diseases is unknown. Therefore, a need exists for studying various forms of PSA and their association with different prostate tissues and diseases. A need also exists for developing a method to distinguish BPH from PCa.

SUMMARY OF THE INVENTION

It is an object of the present invention to determine the source of variable forms of PSA in serum. It is also an object of the present invention to study any associations of different forms of PSA with different prostate tissue or prostate diseases. It is a further object of the present invention to provide a sensitive method for distinguishing BPH from prostate cancer.

These and other objects and advantages are achieved in the present invention by focusing the study on prostate tissues as the source of variable forms of PSA in serum, since PSA is thought to result from retrograde release of PSA from the prostate into the serum (11). In order to determine what molecular forms of PSA are present in the prostate, the present invention has examined three different types of prostate tissue: 1) non-cancerous peripheral zone tissue (PZ-N); 2) cancerous peripheral zone tissue containing at least 80% tumor (PZ-C); and 3) non-cancerous transition zone tissue (TZ). It is the TZ which becomes hyperplastic in patients with BPH. In contrast, most cancers are found in the peripheral zone (PZ).

From these studies, the present invention has identified two subsets of free PSA which are differentially elevated in prostate TZ and PZ. It is believed that the measurement of these free forms of PSA may help distinguish BPH and PCa in patients with prostate disease.

Accordingly, one aspect of the present invention provides a method for determining different forms of prostate specific antigen (PSA) contained in a sample comprising:
 (a) determining the amount of proPSA contained in the sample;
 (b) determining the amount of BPSA in the sample; and
 (c) mathematically combining the results of step (a) and step (b).

Another aspect of the present invention provides a diagnostic method for determining the presence of BPH or prostate cancer in a sample comprising the steps of:
 (a) providing a first agent that specifically binds to proPSA;
 (b) providing a second agent that specifically binds to BPSA;
 (c) contacting the first agent and the second agent with the sample under a condition that allows the formation of a first binary complex comprising the first agent and the proPSA and a second binary complex comprising the second agent and the BPSA;
 (d) detecting or determining the presence or amount of the first and second complexes;
 (e) mathematically combining the amount of the first and second complexes, or the amount of proPSA and the amount of BPSA; and
 (f) relating the combination to the presence of BPH or prostate cancer in the sample.

A further aspect of the present invention provides a diagnostic kit for determining the presence of BPH or prostate cancer in a sample comprising:
 (a) a known amount of a first agent which specifically binds to a proPSA; and
 (b) a known amount of a second agent which specifically binds to a BPSA,
  wherein the first and the second agents, respectively, comprise a detectable label or binds to a detectable label.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which:

FIG. 3A shows that the BPSA (15%) elutes at 8 min and the other forms of PSA elute at 10 min. FIG. 3B shows the HIC-HPLC purified BPSA and PSA.

FIG. 6 is the linear sequence of amino acids for PSA; The arrows show the sites of internal peptide bond cleavage which are described in the text.

DETAILED DESCRIPTION OF THE INVENTION

Figure 1:
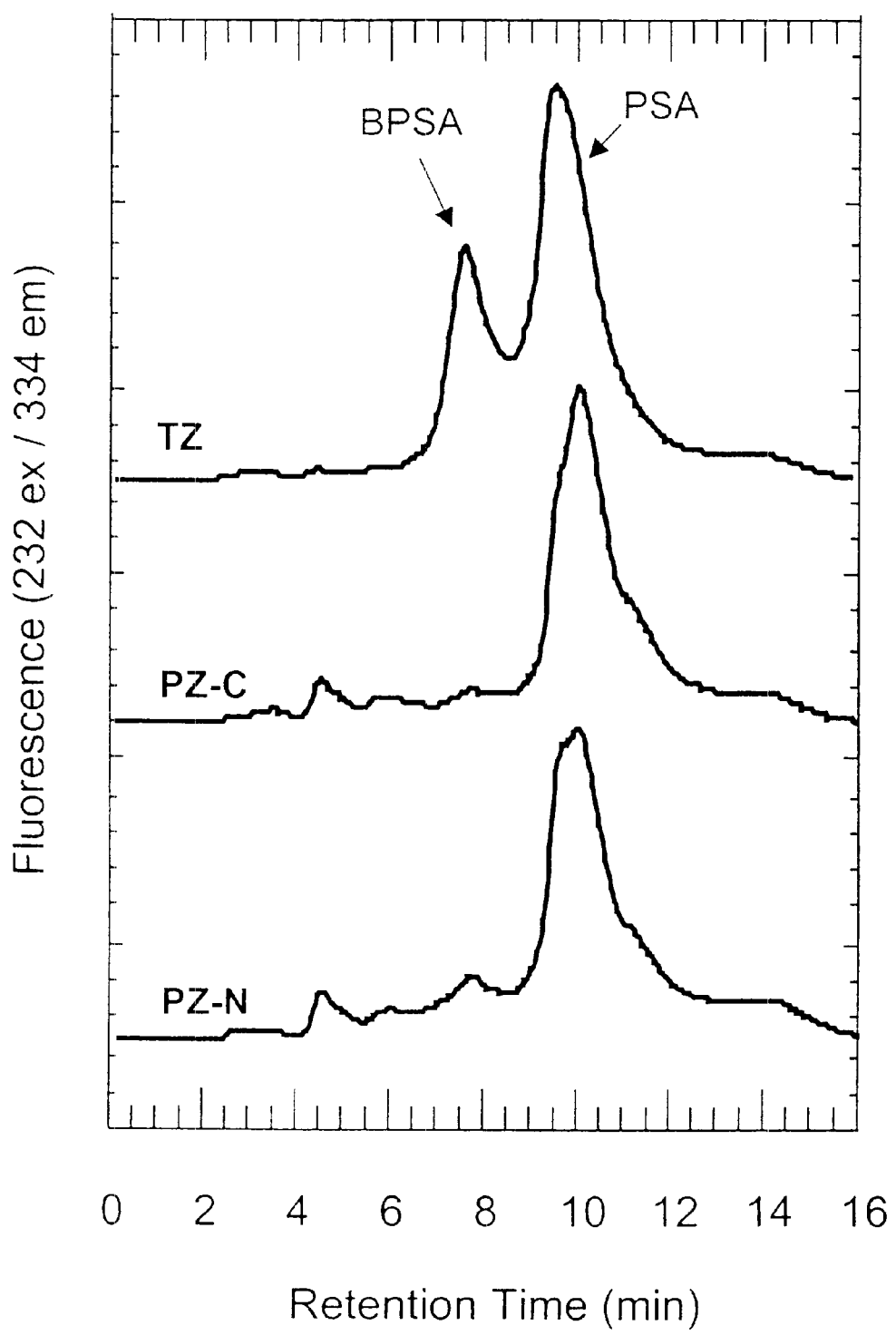
FIG. 1 is a high-performance hydrophobic interaction chromatographic profile of immunoaffinity-purified PSA isolated from prostate tissues. Three matched tissues from the same prostate were analyzed: transitional zone, TZ; peripheral zone containing 80–100% tumor, PZ-C; peripheral zone with no cancer, PZ-N.

The present invention is based on the unexpected discovery that different forms of PSA are associated with different prostate tissues or different prostate diseases.

The prostate is composed of three zones: the central zone, the peripheral zone (PZ) and the transition zone (TZ). The PZ comprises about 70% of the volume of a normal prostate, while the central zone and TZ are about 25% and 5%, respectively. All three zones are well defined in the art. (See *Biopsy Pathology of the Prostate*, David G. Bostwick and Paul A. Dundore, published by Chapman & Hall USA, 115 Fifth Ave., New York, N.Y., 10003.) Briefly, the TZ is characterized by small, simple glands embedded in a compact stroma, whereas the PZ is characterized by small glands embedded in a loose stroma. The TZ tissue forms a distinctive boundary with the PZ. The PZ and TZ are the zones of primary interest, since cancer is localized primarily to the PZ, while BPH is the result of tissue enlargement of the TZ. With extensive BPH, the TZ grows to several times the volume of other prostate zones. The TZ tissue surrounds the proximal prostate urethra, which is the reason that restricted urinary flow is a symptom of enlarged TZ resulting from BPH.

It is a discovery of the present invention that proPSA exists in PZ at an elevated level. It is also a discovery of the present invention that BPSA exists in TZ at an elevated level. Since cancer is localized primarily to the PZ, and BPH is the result of tissue enlargment of the TZ, the present invention discovers that the ratio of proPSA and BPSA may be used as a marker to distinguish BPH from prostate cancer tissues.

Accordingly, one aspect of the present invention provides. a method for determining a ratio of different forms of prostate specific antigen (PSA) in a sample. The method includes:

(a) determining the amount of proPSA contained in the sample;

(b) determining the amount of BPSA in the sample; and (c) mathematically combining the amount of proPSA and the amount of BPSA.

The term "proPSA" or "pPSA" as used herein refers to a precursor form of PSA. A full-length precursor form of PSA includes a propeptide of 7 amino acids, APLILSR, identified as SEQ ID NO:1, which precedes the mature PSA protein of 237 amino acids. The full-length amino acid sequence of a proPSA is known in the art and is fully described in the reference (15), the relevant content of which is incorporated herein by reference. For the purpose of the present invention, the last amino acid "R" of the propeptide sequence is counted as [−1] amino acid. For example, [−7] proPSA is a proPSA with its terminus starting at −7aa of the propeptide. It contains the full-length proPSA. [−5] proPSA indicates that the terminus of the proPSA starts at −5aa of the propeptide, and it contains the last five amino acid sequence of the propeptide sequence of proPSA, etc. For the purpose of the present invention, proPSA of the present invention includes both full-length and truncated forms of proPSA with its terminus started at any amino acid of the propeptide of the proPSA. Examples of proPSA of the present invention include, but are not limited to, [−1]pPSA, [−2]pPSA, [−4]pPSA, [−5]pPSA and [−7]pPSA.

A proPSA of the present invention, particularly [−2] proPSA and [−4]proPSA, exists at an elevated level in the peripheral zone compared to the transition zone of prostate tissue. For the purpose of the present invention, the level of proPSA is elevated if the percentage of the proPSA compared to total PSA is higher than the percentage of the proPSA occurring in the transition zone of prostate tissues. In accordance with one embodiment of the present invention, proPSA extracted from prostate tissues contains up to 35% of proPSA of the present invention. The proPSA is lower or absent in the transition zone. Since prostate cancer is located primarily in the PZ, and any PSA leaking into the serum due to a neoplastic lesion would be expected to contain the population of PSA in the PZ, it is believed that proPSA may be used as a marker associated with prostate cancer.

The proPSA is inactive, i.e., it lacks chymotrypsin-like enzymatic activity and therefore is present in serum as free PSA, not as PSA antichymotrypsin complex. For the purpose of the present invention, a free PSA is a PSA that is not complexed as part of an antichymotrypsin complex.

ProPSA of the present invention may be made by methods commonly known in the art, such as, but not limited to, protein purification techniques, recombinant protein techniques, and protein synthesis techniques. The details for producing and detecting proPSA of the present invention are discussed in a co-pending U.S. patent application entitled "Forms of Prostate Specific Antigen and Methods for Their Detection," filed concurrently herewith, which is a continuation-in-part of U.S. application Ser. No. 08/846,408,the relevant content which are incorporated herein in their entirety.

The term "BPSA" as used herein refers to a form of PSA that comprises at least one clip at Lys 182 of the amino acid sequence of a mature form of PSA. A mature form of PSA has 237 amino acid residues with a molecular mass of 28,400 D (13) and the amino acid sequence is fully described in references (14). The sequence of the matured form of PSA is shown in FIG. 6. the sequence of which is identified as SEQ ID NO:2A BPSA of the present invention has at least one clip at Lysine 182 of the amino acid sequence of a mature form of PSA. In other words, a BPSA of the present invention has the same amino acid sequence of a mature form of PSA, except that the polypeptide chain of the PSA of the present invention has been hydrolyzed between residues 182 and 183.In accordance with embodiments of the present invention, a BPSA of the present invention may also include an additional one or more clips at Ile 1, Lys145 and Lys146 of the amino acid sequence of a mature PSA. In one embodiment of the present invention, a BPSA of the present invention consists of two clips at Lys145 and Lys182.

A BPSA of the present invention exists at an elevated level in the transition zone of BPH tissue, compared to peripheral zone cancer and non-cancer prostate tissues. For the purpose of the present invention, the level of BPSA is elevated if the percentage of the BPSA compared to total PSA is higher than the percentage of the BPSA occurring in peripheral zone cancer and non-cancer prostate tissues. In accordance with one embodiment of the present invention, PSA extracted from BPH tissues contains from 5 to 30% of BPSA of the present invention. The BPSA are lower or absent in peripheral zone cancer and non-cancer prostate tissues. Since it is the TZ which becomes hyperplastic in patients with BPH, it is believed that BPSA of the present invention may be specific for BPH.

The BPSA is inactive, i.e., it lacks chymotrypsin-like enzymatic activity and therefore is present in serum as free PSA, not as PSA antichymotrypsin complex. For the purpose of the present invention, a free PSA is a PSA that is not complexed as part of an antichymotrypsin complex.

The BPSA of the present invention may be isolated from tissues or seminal plasma or prepared by in vitro trypsin treatment by methods described herein or otherwise known in the art. BPSA of the present invention may be separated from other forms of PSA by HIC-HPLC technique, a technique that is well known in the art. BPSA of the present invention forms a major peak by HIC-HPLC. Details of isolation or preparation methods for BPSA are described in a co-pending U.S. Application filed concurrently with the present application, which application is entitled "Novel Forms of Prostate Specific Antigen (PSA) Specific for Benign Prostatic Hyperplasia (BPH) and Methods of Using Such," the relevant content of which is incorporated herein in its entirety by reference.

ProPSA and BPSA of the present invention may be characterized and used for antibody development. The pending U.S. patent application Ser. No. 08/846,408 describes in detail the antibodies and methods of developing antibodies, particularly monoclonal antibodies against proPSA of the present invention, the relevant content of which is incorporated herein in its entirety by reference. The co-pending U.S. Patent Application entitled "Novel Forms of Prostate Specific Antigen (PSA) Specific for Benign Prostatic Hyperplasia (BPH) and Methods of Using Such," which is filed concurrently with the present application, describes in detail the antibodies and methods of making antibodies, particularly monoclonal antibodies against BPSA of the present invention, the relevant content of which is incorporated herein in its entirety by reference.

Briefly, an antibody which consists essentially of pooled monoclonal antibodies with different epitopic specificities, as well as distinct monoclonal antibody preparations, is provided. Monoclonal antibodies are made from an antigen containing the novel form of PSA of the present invention or fragments thereof by methods well known in the art (E. Harlow et al., Antibodies: *A Laboratory Manual*, Cold Spring Harbor Laboratory, 1988). In general, this method involves preparing an antibody-producing fused cell line, e.g., from primary spleen cells fused with a compatible continuous line of myeloma cells, growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of antibodies are also within the scope of the present invention, e.g., the f(ab) fragment, as are partially humanized monoclonal antibodies.

If desired, polyclonal antibodies can be further purified, for example, by binding to elution from a matrix to which a polypeptide or a peptide to which the antibodies were raised is bound. Those skilled in the art will know of various techniques common in the immunology arts for purification and/or concentration of polyclonal antibodies, as well as monoclonal antibodies. (See, for example, Coligan et al., Unit 9, *Current Protocols in Immunology*, Wiley Interscience, 1991, incorporated by reference.)

The term "antibody" as used in this invention includes intact molecules as well as fragments thereof, such as Fab, $F(ab')_2$ and Fv, which are capable of binding the epitopic determinant. These antibody fragments retain some ability to selectively bind with its antigen or receptor.

Accordingly, one aspect of the present invention provides an antibody that is specifically immunoreactive with and binds to proPSA or BPSA in the present invention. The term "specifically immunoreactive or specifically bind to" as used herein indicates that the antibodies of the present invention preferentially recognize and bind to proPSA or BPSA than other forms of PSA, such as other clipped or non-clipped mature forms of PSA. The term "preferentially recognize and bind" as used herein means that the antibodies of the present invention bind to proPSA or BPSA of the present invention to a greater extent than binding to other forms of PSA under the same conditions. Examples of monoclonal antibodies that preferentially bind to proPSA include, but are not limited to, PS1Z134, PS1Z120, PS1Z125 and PS1Z80. Examples of monoclonal antibodies that preferentially bind to BPSA include, but are not limited to, PS2C109, PS2C501, PS2C634, PS2C807 and PS2C837.

Antibodies of the present invention may be used for detecting and determining the presence and amount of proPSA or BPSA in a sample. In accordance with the present invention, the proPSA and BPSA may be detected in patient tissue samples by immunohistochemical methods and/or in patient fluid samples by in vitro immunoassay procedures.

Immunohistochemical methods for the detection of antigens in patient tissue specimens are well known in the art and need not be described in detail herein. For example, methods for the immunohistochemical detection of antigens are generally described in Taylor, *Arch. Pathol. Lab. Med.* 102:113 (1978). Briefly, in the context of the present invention, a tissue specimen obtained from a patient suspected of having a prostate-related problem is contacted with an antibody, preferably a monoclonal antibody, recognizing either proPSA or BPSA. The site at which the antibody is bound is thereafter determined by selective staining of the tissue specimen by standard immunohistochemical procedures. The same procedure may be repeated on the same sample using another antibody that recognizes BPSA or proPSA. Alternatively, a sample may be contacted with an antibody against proPSA and an antibody against BPSA simultaneously, provided that the antibodies are labeled differently or are able to bind to a different label. In one embodiment of the present invention, the tissue specimen is a tissue specimen obtained from the prostate of a patient. The prostate tissue may be a normal prostate tissue, a cancer prostate tissue or a benign prostatic hyperplasia tissue.

Similarly, the general methods of the in vitro detection of antigenic substances in patient fluid samples by immunoassay procedures are also well known in the art and require no repetition herein. For example, immunoassay procedures are generally described in Paterson et al., Int. J. Can. 37:659 (1986) and Burchell et al., Int. J. Can. 34:763 (1984). According to one embodiment of the present invention, an immunoassay for detecting proPSA and BPSA in a biological sample comprises the steps of: (a) contacting an amount of a first agent which specifically binds to proPSA with the sample under a condition that allows the formation of a binary complex comprising the first agent and the proPSA and (b) detecting or determining the presence or amount of the complex as a measure of the amount of the proPSA; or (a) contacting an amount of a second agent which specifically binds to BPSA with the sample under a condition that allows the formation of a binary complex comprising the second agent and the BPSA and (b) detecting or determining the presence or amount of the complex as a measure of the amount of the BPSA contained in the sample. Alternatively, a sample may be contacted by the first and the second agents simultaneously, provided that the agents may be labeled differently or are capable of binding to different labels.

For the purpose of the present invention, the biological sample can be any human physiological fluid sample that contains either proPSA or BPSA of the present invention. Examples of the human physiological fluid sample include, but are not limited to, serum, seminal fluid, urine and plasma.

For the purpose of the present invention, both monoclonal antibodies and polyclonal antibodies may be used as long as such antibodies possess the requisite specificity for the antigen provided by the present invention. Preferably, monoclonal antibodies are used.

Monoclonal antibodies can be utilized in liquid phase or bound to a solid phase carrier. Monoclonal antibodies can be bound to many different carriers and used to determine the novel form of PSA of the present invention. Examples of well-known carriers include glass, polystyrene, polypropylene, polyethylene, dextran, nylon, amylases, natural and modified celluloses, polyacrylamides, agaroses and magnetites. The nature of the carrier can be either soluble or insoluble for purposes of the invention. Examples of insoluble carriers include, but are not limited to, a bead and a microtiter plate. Those skilled in the art will know of other suitable carriers for binding monoclonal antibodies, or will be able to ascertain such under routine experimentation.

In addition, the monoclonal antibodies in these immunoassays can be detectably labeled in various ways. For example, monoclonal antibodies of the present invention can be coupled to low molecular weight haptens. These haptens can then be specifically detected by means of a second reaction. For example, it is common to use such haptens as biotin, which reacts with avidin, or dinitrophenyl, pyridoxal and fluorescein, which can react with specific antihapten antibodies. In addition, monoclonal antibodies of the present invention can also be coupled with a detectable label such as an enzyme, radioactive isotope, fluorescent compound or metal, chemiluminescent compound or bioluminescent compound. Furthermore, the binding of these labels to the desired molecule can be done using standard techniques common to those of ordinary skill in the art.

One of the ways in which the antibody can be detectably labeled is by linking it to an enzyme. This enzyme, in turn, when later exposed to its substrate, will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase and acetylcholine esterase.

For increased sensitivity in the ELISA system, the procedures described can be modified using biotinylated antibodies reacting with avidin-peroxidase conjugates.

The amount of antigen can also be determined by labeling the antibody with a radioactive isotope. The presence of the radioactive isotope would then be determined by such means as the use of a gamma counter or a scintillation counter. Isotopes which are particularly useful are $^3$H, $^{125}$I, $^{123}$I, $^{32}$P, $^{35}$S, $^{14}$C, $^{51}$Cr, $^{36}$Cl, $^{57}$Co, $^{58}$Co, $^{59}$Fe, $^{75}$Se, $^{111}$N, $^{99}$mTc, $^{67}$Ga and $^{90}$Y.

Determination of the antigen is also possible by labeling the antibody with a fluorescent compound. When the fluorescently labeled molecule is exposed to light of the proper wave length, its presence can then be detected due to fluorescence of the dye. Among the most important fluorescent labeling compounds are fluorescein isothiocyanate, rhodamine, phycoerythrin, phycocyanin, allophycocyanin, o-phthaldehyde and fluorescamine.

Fluorescence-emitting metal atoms such as Eu (europium), and other lanthanides, can also be used. These can be attached to the desired molecule by means of metal-chelating groups, such as DTPA or EDTA.

Another way in which the antibody can be detectably labeled is by coupling it to a chemiluminescent compound. The presence of the chemiluminescent-tagged immunoglobulin is then determined by detecting the presence of luminescence that arises during the course of a chemical reaction. Examples of particularly useful chemiluminescent labeling compounds are luminol, isoluminol, aromatic acridinium ester, imidazole, acridinium salt and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labeling are luciferin, luciferase and aequorin.

Qualitative and/or quantitative determinations of proPSA and BPSA of the present invention in a sample may be accomplished by competitive or non-competitive immunoassay procedures in either a direct or indirect format.

Examples of such immunoassays are the radioimmunoassay (RIA) and the sandwich (immunometric) assay. Detection of the antigens using the monoclonal antibodies of the present invention can be done utilizing immunoassays which are run in either the forward, reverse or simultaneous modes, including immunohistochemical assays on physiological samples. Those skilled in the art will know, or can readily discern, other immunoassay formats without undue experimentation.

The term "immunometric assay" or "sandwich immunoassay" includes a simultaneous sandwich, forward sandwich and reverse sandwich immnunoassay. These terms are well understood by those skilled in the art. Those skilled in the art will also appreciate that antibodies according to the present invention will be useful in other variations and forms of assays which are presently known or which may be developed in the future. These are intended to be included within the scope of the present invention.

Because BPSA is preferentially elevated in TZ and pPSA is elevated in PZ, the combination of these two subforms of free PSA may lead to improved discrimination between BPH and PCa. It is the TZ which becomes hyperplastic in patients with BPH, whereas most cancers are found in the PZ. Therefore, the mathematical combination of the amount of proPSA and BPSA may be used as a serum marker or as an immunohistological marker to help distinguish BPH from prostate cancer, although it should be noted that proPSA and BPSA alone may also be used as a serum marker or as an immunohistological marker for distinguishing BPH from prostate cancer. The term "mathematical combination" as used herein refers to any mathematical caculation of the amount of proPSA and BPSA. In one embodiment, the mathematical combination is a ratio. The ratio of proPSA and BPSA in a sample may be determined by comparing the amount of proPSA or proPSA complex to the amount of BPSA or BPSA complex in the sample.

Accordingly, another aspect of the present invention provides a diagnostic method for determining the presence of BPH or prostate cancer in a sample comprising the steps of:
(a) providing a first agent that specifically binds to proPSA;
(b) providing a second agent that specifically binds to BPSA;
(c) contacting the first agent and the second agent with the sample under a condition that allows the formation of a first binary complex comprising the first agent and the proPSA and a second binary complex comprising the second agent and the BPSA;
(d) detecting or determining the presence or amount of the first and second complexes;
(e) mathematically combining the amount of the first and the second complexes or the amount of proPSA and the amount of BPSA; and
(f) relating the combination to the presence of BPH or prostate cancer in the sample.

In accordance with embodiments of the present invention, the agents comprise antibodies, particularly monoclonal antibodies of the present invention. Preferably, when a sample is contacted with the first and the second agents, the first and the second agents may be labeled differently or are able to bind to different labels to form respective complexes that may be detected separately. Alternatively, the sample may be contacted with one agent first so that either proPSA or BPSA may be detected first, then the same sample may be contacted with another agent in order to detect another form of PSA.

In one embodiment of the present invention, the sample may be a sample of human physiological fluid such as, but not limited to, serum, seminal plasma, urine and plasma. In another embodiment of the present invention, the sample may be tissue specimen from the prostate of a patient. For the purpose of the present invention, the agent may be an antibody, particularly a monoclonal antibody of the present invention. In one embodiment of the present invention, the mathematical combination is a ratio.

Another aspect of the present invention also provides a diagnostic kit for determining the presence of BPH or prostate cancer in a sample. The kit includes:
(a) a known amount of a first agent which specifically binds to a proPSA,
(b) a known amount of a second agent which specifically binds to a BPSA,
    wherein the first and the second agents, respectively, comprise a detectable label or bind to a detectable label.

For the purpose of the present invention, the sample may be a sample of human physiological fluid such as, but not limited to, serum, seminal plasma, urine or plasma. The sample may also be a tissue specimen coming from the prostate of a patient. The agent may be an antibody, particularly a monoclonal antibody of the present invention. Preferably, the first and the second agents, respectively, comprise a different detectable label or bind to a different detectable label.

Since proPSA or BPSA alone may be used as a serum marker or as an immunohistological marker for distinguishing BPH from prostate cancer, the present invention also provides a diagnostic method for distinguishing BPH from prostate cancer by detecting and determining the amount of proPSA or BPSA in a sample. The amount of either proPSA or BPSA may be determined in patient tissue samples by immunohistochemical methods and/or in patient fluid samples by in vitro immunoassay procedures described herein.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Materials and Methods

Isolation of PSA from Prostate Tissue

Prostate tissue was frozen in liquid nitrogen and pulverized to a fine powder in a metal tissue pulverizer maintained in liquid nitrogen. For the PZ-N, PZ-C and TZ tissue samples, which ranged from 100–300 mg, the frozen tissue powder was homogenized in 3 mils of PBS containing a protease inhibitor cocktail (Complete, Boehringer Manheim) using a glass tissue homogenizer. The sample was then centrifuged to remove cell debris and the supernatant solution filtered through a 0.2 um membrane. Larger amounts of tissue were extracted as described above except that the tissue was homogenized in a 50 ml tube using a Polytron tissue homogenizer.

PSA was purified from the filtered supernatant solution by passage over an immunoaffinity column containing bound anti-PSA mAb, PSM773, at 5 mg per ml of resin. The column was washed with 40 volumes of PBS containing 0.1% reduced Triton-X100, and the PSA eluted with 100 mM glycine pH 2.5, containing 200 mM sodium chloride. The eluant was immediately neutralized with 10% vol/vol IM Tris pH 8.0.

Preparation of BPSA In Vitro

Processed, filtered seminal plasma was diluted 1:10 in PBS and passed over an immunoaffinity column with bound anti-PSA mAb, PSM773. The column was washed with 20 volumes of PBS containing 0.1% reduced Triton X100, and the PSA eluted with 100 mM glycine pH 2.5 containing 200 mM sodium chloride. The purified PSA was applied to HIC-HPLC as described below, and the 8 min BPSA peak and the 10 min PSA peak were collected separately. The PSA from the 10 min peak was dialyzed into 100 mM Tris, pH 8 and incubated with 1% w/w trypsin for 30 min at 37° C. The trypsin in the mixture was inactivated by addition of a mass of aprotinin equal to twice the added trypsin. The incubation mixture was applied to HIC-HPLC and the resultant clipped PSA peak were collected for analysis.

HIC-HPLC of PSA

High-performance hydrophobic interaction chromatography (HIC-HPLC) was performed using a polypropylaspartamide column (PolyLC, distributed by Western Analytical, Temecula, Calif.). The column was 4.6×250 mm in length with a 1000 Å pore size. Samples were applied in 1.5 M ammonium sulfate and eluted with a gradient. Buffer A: 1.2 M sodium sulfate, 25 mM sodium phosphate, pH 6.3, and Buffer B: 50 mM sodium phosphate, 5% v/v 2-propanol. The gradient was 0–35 % B 1 min, 30–80% B 12 min, isocratic at 80% B for 2 min before equilibration in Buffer A. High-sensitivity peak detection was obtained with a Varian Model 9070 scanning fluorescence detector using an excitation of 232 nm and emission of 334 nm to detect the tryptophan residues in protein.

Amino Acid Sequencing of PSA

N-terminal sequence analysis of the samples was performed on a PE-Applied Biosystems Model 492 amino acid sequencer (Perkin-Elmer, Applied Biosystems Division, Foster City, Calif.). Purified PSA and peaks collected by HIC-HPLC were applied directly to Prosorb cartridges (Perkin-Elmer, Applied Biosystems Division, Foster City, Calif.), washed 3× with 0.1 mL 0.01% trifluoroacetic acid and applied to the Model 492 sequencer.

Generation of Monoclonal Antibodies to pPSA ProPSA was purified from the medium of AV12 by the use of immunoaffinity chromatography using the anti-PSA antibody, PSM773. The AV12 cells expression proPSA were generated as described in the pending U.S. patent application Ser. No. 08/846,408. The mice were immunized once with 50 ug of blocked immunogen in CFA and twice with 25 ug of blocked immunogen in IFA. The hybridoma was generated according to reported procedures (16). The culture supernatant was screened for reactivity against pPSA.

Alternatively, the mice were immunized once with 50 ug of mutant proPSA 217 ser-gly immunogen in CFA and twice 25 ug of same immunogen in IFA.

Hybridoma Screening Assays 50 ul of culture supernatant was added to the wells of streptavidin microplate (Wallac, Turku, Finland) and 50 ul of biotinylated pPSA at 100 ng/ml was also added. After 1 hr incubation the plate was washed with PBS/0.1% tween-20, then incubated with 50 ul per well of goat anti-mouse Ig horseradish peroxidase (1:10,000) diluted in PBS/1% BSA and 0.1% tween-20. After 1 hr incubation, the plate was washed and developed with OPD substrate. To determine the specificity of monoclonal antibodies, the reactivity of 100 ng/ml pPSA and 100 ng/ml intact PSA was compared.

Results

BPSA in Prostate Tissues by HIC-HPLC

PSA was immunoaffinity purified from tissue extracts using the anti-PSA monoclonal antibody, PSM773, and then further resolved by high-performance hydrophobic interaction chromatography (HIC-HPLC). A second, smaller peak of PSA was observed in some samples, which eluted earlier than the main PSA peak. It was determined that this variant form of PSA was elevated primarily in TZ tissues compared to PZ tissues. FIG. 1 shows the comparative HIC-HPLC profile of the PSA purified from matched zones of prostate tissue. Three matched tissues from the same prostate were analyzed: transitional zone, TZ; peripheral zone containing 80–100% tumor, PZ-C; peripheral zone with no cancer, PZ-N. Normally, PSA eluted at 10 min under these chromatographic conditions. In this example, the PSA peak eluting at 8 min contains 28% of the total PSA in the TZ extract, while it is present at only 3% and 8% in the PZ-C and PZ-N tissues, respectively.

Figure 2:
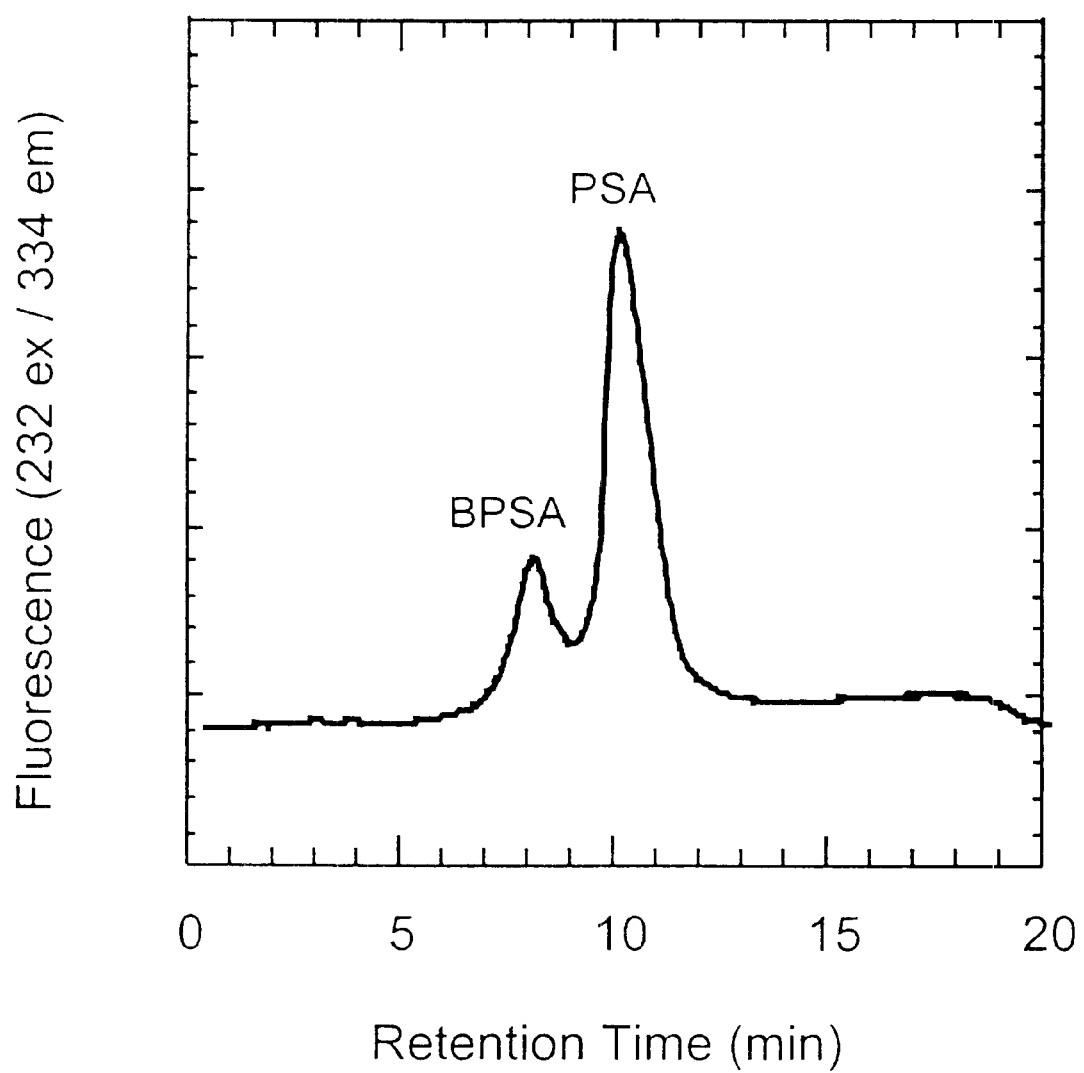
FIG. 2 is HIC-HPLC profile of PSA purified from TURP prostate tissue. The BPSA (22%) elutes at 8 min and the other forms of PSA elute at 10 min.

For the purpose of the present invention, the PSA eluting at 8 min has been designated as BPSA. Since the absolute value of BPSA was seen to vary between 5 and 30% of the total PSA in different TZ patient samples, the present invention also examined TURP tissue. The TURP procedure is performed on patients with BPH. The TURP procedure removes the transition zone and so a PSA analysis of a TURP extract from a single patient provides an average level of BPSA throughout the entire TZ. FIG. 2 shows the HIC-HPLC profile of the PSA purified from TURP tissue. BPSA represented 22% of the total PSA in this sample. From the eight different TURP samples tested, six of the TZ tissues contained high levels of BPSA, with an average of 20% ±3% of the total PSA. Two of the TURP samples had low BPSA, with an average of 3.2% ±0.5%.

Control experiments were performed on tissue extracts wherein an aliquot of the extract was removed and incubated at 37° C. for 1 hr to determine if any additional internal cleavage occurred. No additional internal cleavage sites were obtained after incubation, as determined by HIC-HPLC and N-terminal sequencing of the subsequently purified PSA (data not shown). This indicates that there is no significant in vitro proteolytic cleavage during the extraction and PSA purification procedure, and that any observed PSA clips are endogenous to the PSA prior to purification and analysis.

Characterization of BPSA from Prostate Tissue

Figure 3:
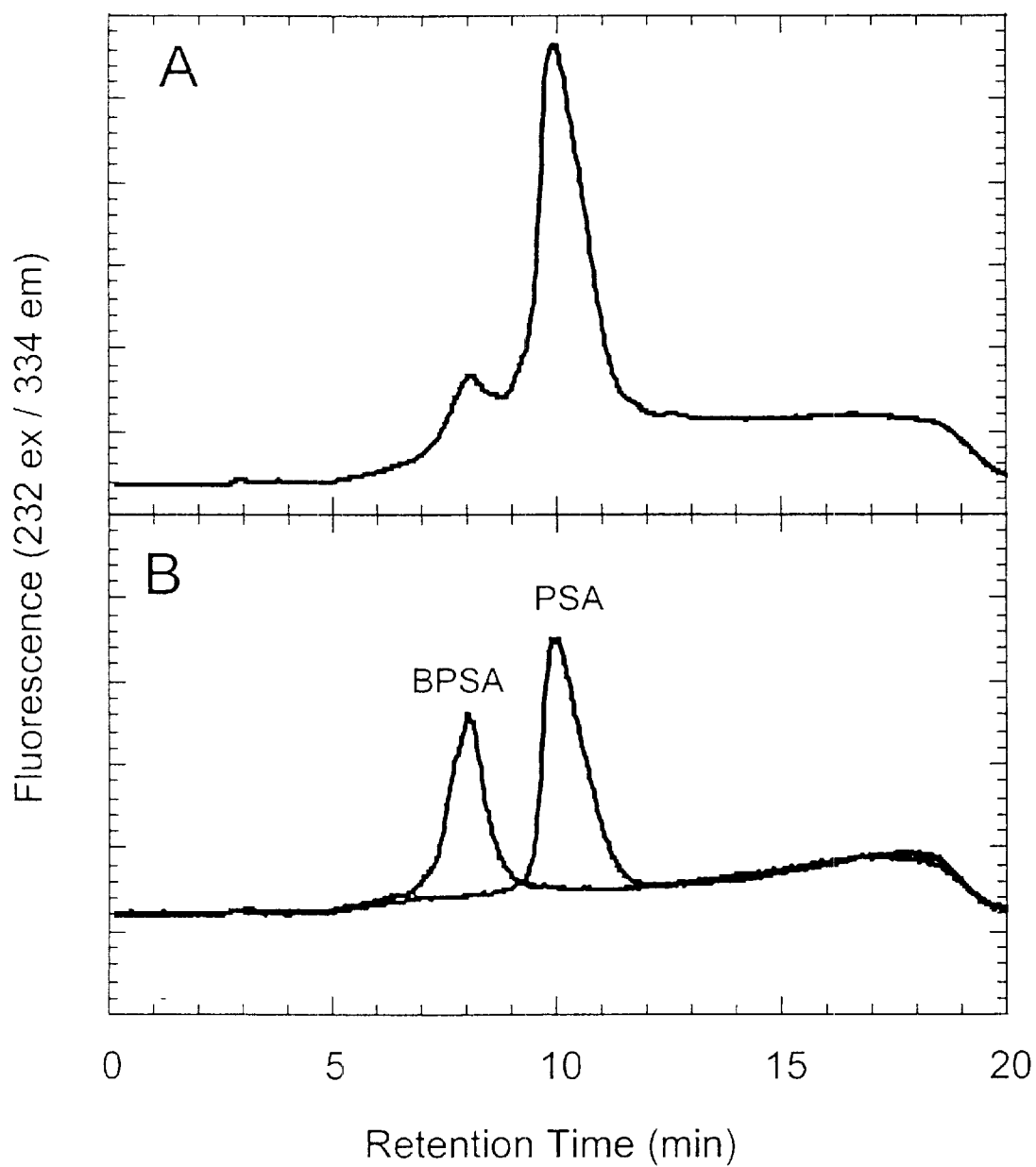
FIG. 3 is HIC-HPLC profile of PSA purified from prostate tissue.

Approximately 50 g of prostate tissue obtained from prostatectomy (n>40) was extracted in order to obtain quantities sufficient for further analysis. These tissues were not characterized as having derived from either the TZ or PZ. FIG. 3A shows the HIC-HPLC profile of the PSA purified from this tissue, which contains approximately 15% BPSA. The 8 min BPSA peak and the 10 min PSA peak were collected individually and analyzed by N-terminal sequencing. FIG. 3B shows that the HIC-HPLC purified BPSA and PSA were cleanly resolved from one another.

Table 1 shows the percentage of internal clips present in each form of PSA. Five main cleavage sites were detected: Ile1, Arg85, Lys145, Lys146 and Lys182. The sequence comparison of these two peaks is distinctive in two ways: 1) the 8 min peak contains a high percentage of internal clips including a distinctive clip at Lys 182; and 2) the majority of the PSA eluting at 10 min contains only minor levels of internal clips.

TABLE 1

|  | % 1 | % 85 | % 145 | % 146 | % 182 |
| --- | --- | --- | --- | --- | --- |
| BPSA, 8 min peak | 32 | 0 | 52 | 11 | 78 |
| PSA, 10 min peak | 7 | 0 | 13 | 2 | 5 |

The clip at Lys182 is the most distinctive feature of the 8 min BPSA peak and appears to be responsible for the shift from 10 min to 8 min. The clip at Ile1, which generates PSA beginning with N-terminus valine, is also elevated in BPSA. The Ile1 clip, as well as the Lys146 clip, have been reported in the PSA obtained from BPH nodules (9). The clip at Lys145 is the primary internal cleavage site in PSA purified from seminal plasma. PSA clipped only at Lys145 continues to elute at 10 min (data not shown). Thus, BPSA represents a different form of inactive PSA than has been characterized from seminal plasma.

The Distribution of BPSA in Tissues

The PSA from 18 sets of matched prostate tissues was examined: 10 from large volume prostates (>50 g) and 8 small volume prostates (<20 g). The percentage of the total PSA present as BPSA is shown in Table 2. In the majority of the samples, the TZ contains elevated levels of BPSA compared to the matched PZ tissues. There is no apparent difference between the large and small volume prostates.

TABLE 2

| | Large Volume Prostate (>50 g) | | | | Small Volume Prostate (<20 g) | | |
|---|---|---|---|---|---|---|---|
| # | PZ-N | PZ-C | TZ | # | PZ-N | PZ-C | TZ |
| 1 | 3.5 | 5.6 | 12.0 | 11 | 1.7 | 0.0 | 6.5 |
| 2 | 3.5 | 5.6 | 10.8 | 12 | 0.0 | 0.0 | 29.5 |
| 3 | 0.0 | 4.7 | 5.3 | 13 | 3.2 | 4.0 | 4.8 |
| 4 | 3.2 | 13.9 | 6.6 | 14 | 5.0 | 4.6 | 19.0 |
| 5 | 9.7 | 10.7 | 3.8 | 15 | 6.3 | 1.3 | 2.3 |
| 6 | 5.3 | 5.2 | 9.4 | 16 | 5.5 | 4.9 | 1.1 |
| 7 | 0.0 | 2.3 | 7.6 | 17 | 0.9 | 0.0 | 1.7 |
| 8 | 4.0 | 2.5 | 4.4 | 18 | 5.2 | 2.3 | 4.4 |
| 9 | 7.5 | 6.6 | 13.9 | | | | |
| 10 | 8.3 | 3.2 | 28.1 | | | | |

The Measurement of pPSA in Prostate Tissues

Figure 4:
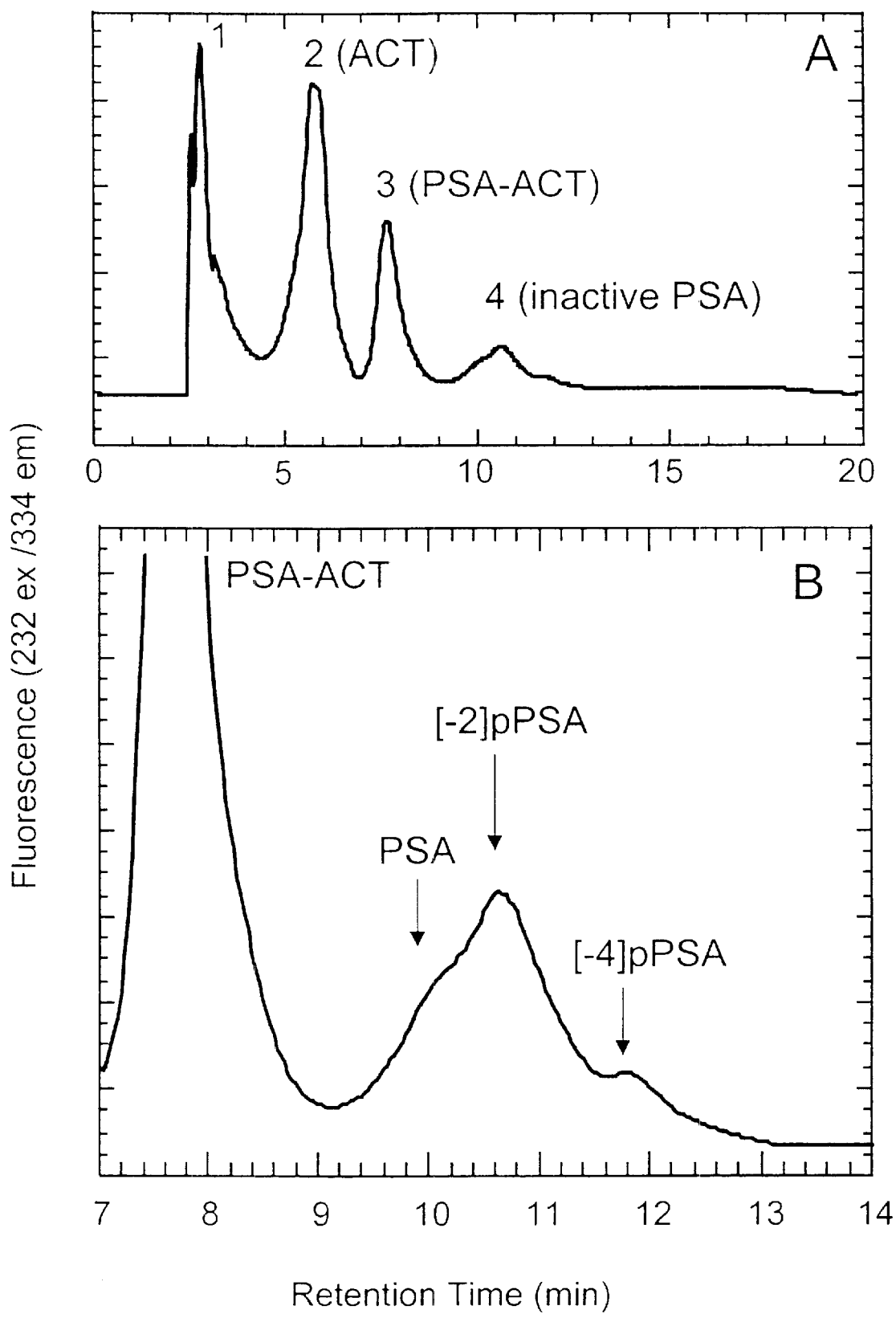
FIG. 4 is HIC-HPLC profile of the reaction mixture of PZ-N PSA incubated with excess ACT. Peak 1 is inactive ACT which has been cleaved by PSA. Peak 2 is the residual excess active ACT. Peak 3 is the covalent PSA-ACT complex. Peak 4 is the inactive PSA which did not react with ACT. 3B is an enlargement of 3A showing the PSA-ACT and inactive PSA peaks. Different fractions of the inactive PSA peak were collected and analyzed by N-terminal sequencing, as indicated by the arrows.

Aside from BPSA, the inactive forms of PSA in tissue extracts include [−1]pPSA, [−2]pPSA, [+4]pPSA, [+5]PSA, PSA clipped at Lys145 and mature inactive PSA. These inactive forms were demonstrated by incubation of PSA with ACT, followed by terminal sequence analysis of the PSA which did not form a complex with ACT. FIG. 4 shows the HIC-HPLC profile of PZ-N PSA incubated with ACT. The original profile of this PZ-N sample is seen in FIG. 1. Peak 1 in FIG. 4 is the inactive clipped ACT formed incubation with PSA (7). Peak 2 is the residual excess active ACT remaining after incubation. Peak 3 is the PSA-ACT complex, and peak 4 is the inactive PSA that did not a complex with ACT. N-terminal sequencing of peak 4, the inactive PSA, is shown in panel B. The front half of the inactive PSA peak contains primarily mature PSA, PSA clipped at Lys145 and PSA clipped after Gly4. The second half of the inactive PSA peak contains the majority of the [−2]pPSA. The [−2]pPSA is a truncated form of pPSA which contains the last two amino acids of the 7 amino acid pro leader peptide. PPSA is expressed with a heptapeptide pro leader sequence consisting of APLILSR. Thus, the [−2] pPSA contains the serine-arginine dipeptide on the N-terminal isoleucine of mature PSA. The minor peak eluting at 12 min contains the [−4]pPSA. The retention time of [−4]pPSA has been reported previously (10). The [−2] pPSA constituted 65% of the inactive PSA in this sample and [−4]pPSA was 6%.

The percentage of pPSA formed in the bulk of the tissue samples was determined not by sequencing the inactive PSA after ACT incubation, but by direct N-terminal sequencing of whole immunoaffinity purified PSA. Table 3 shows the percentage of [−2]pPSA found in these samples. In a few samples, very minor levels of other proforms could be detected in whole PSA but [−2]pPSA was the major pro form. Table 3 shows that pPSA is found primarily in the PZ, both cancerous and non-cancerous. By contrast, only four TZ samples showed measurable pPSA. ProPSA was not detectable in the majority of the TZ samples in Table 3. ProPSA was also not detected in the TURP tissues.

TABLE 3

| | Large Volume Prostate (>50 g) | | | | Small Volume Prostate (<20 g) | | |
|---|---|---|---|---|---|---|---|
| # | PZ-N | PZ-C | TZ | # | PZ-N | PZ-C | TZ |
| 1 | 1 | 2.6 | 0 | 11 | 6 | 4 | 3 |
| 2 | 19 | 3.3 | 10 | 12 | 3.4 | 1 | 0 |
| 3 | 4 | 3 | 1 | 13 | 1 | 4 | 0 |
| 4 | 3.5 | 1 | 0 | 14 | 0 | 11 | 0 |
| 5 | 0 | 0 | 0 | 15 | 0 | 0 | 0 |
| 6 | 0 | 8 | 0 | 16 | 0 | 1.2 | 0 |
| 7 | 0 | 0.5 | 0 | 17 | 0 | 3.6 | 0 |
| 8 | 4 | 3.8 | 2.5 | 18 | 7 | 17 | 0 |
| 9 | 2.5 | 5.4 | 0 | | | | |
| 10 | 21 | 35 | 3.6 | | | | |

The Ratio of ProPSA to BPSA in Prostate Tissues

Figure 5:
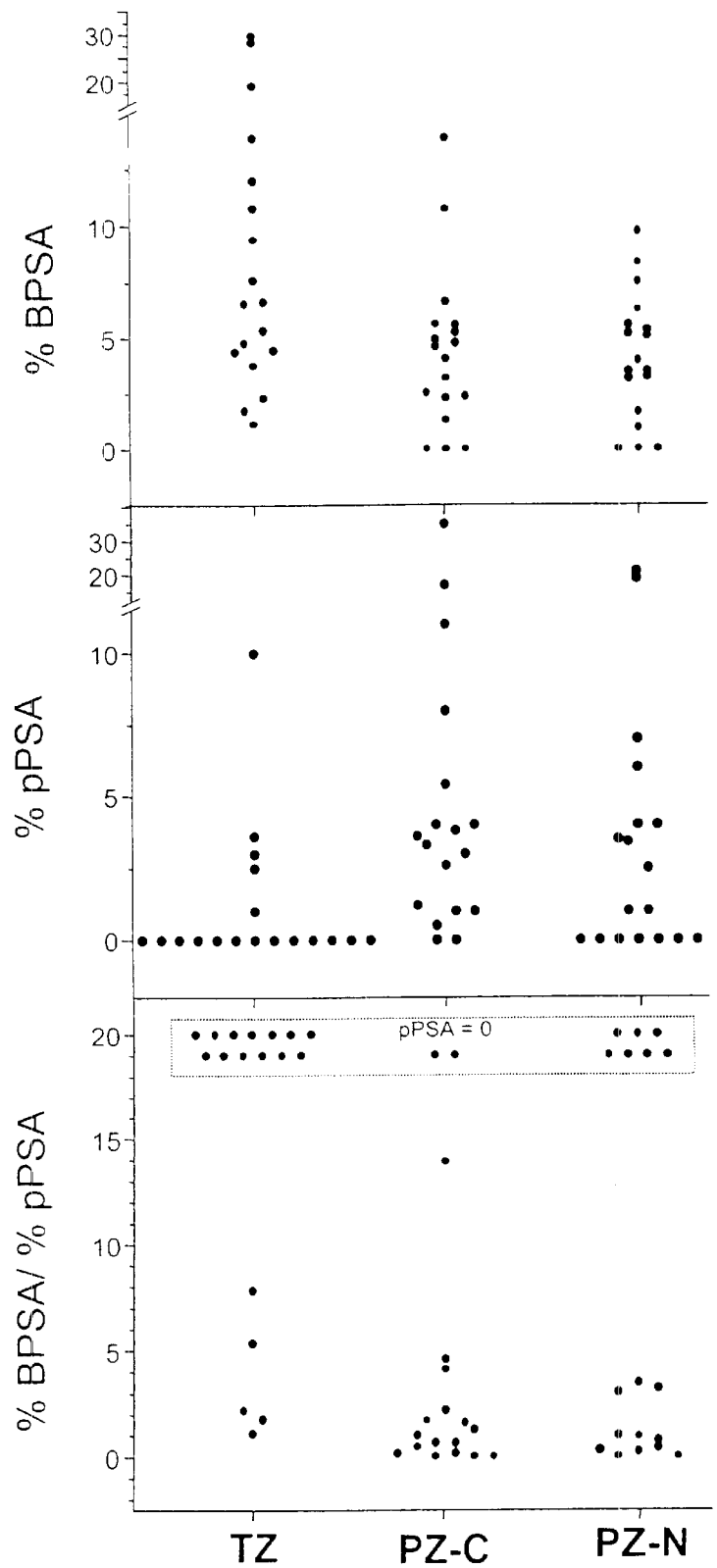
FIG. 5 shows dot plots of BPSA and pPSA in 18 matched sets of prostate tissues. The bottom panel shows the ratio of BPSA/pPSA. TZ, transition zone; PZ-N, peripheral zone-non cancer; PZ-C, peripheral zone-cancer.

Because BPSA is preferentially elevated in TZ and pPSA is elevated in PZ, the combination of these two subforms of free PSA may lead to improved discrimination between BPH and PCa. It is the TZ which becomes hyperplastic in patients with BPH, whereas most cancers are found in the PZ. FIG. 5 shows dot plots of the % BPSA, % pPSA, and the ratio of BPSA/pPSA for the 18 matched tissue samples. FIG. 5 shows a significant discrimination between the TZ and PZ tissues.

Discussion

It is a discovery of the present invention that the TZ tissues contained enriched levels of a specific isoform of PSA which has been designated BPSA. BPSA has a distinctive chromatographic profile by MIC-HPLC and is characterized by at least one clip at Lys182 (Table 1). The finding that BPSA is preferentially elevated in the TZ of cancerous prostates, as well as TURP tissue from non-cancerous prostates, suggests that this form of PSA may be a general marker for PSA derived from the TZ.

Examination of the same set of matched tissues showed a complementary correlation with elevated [−2]pPSA in the PZ tissues. PPSA was largely absent in the TZ. The finding of pPSA associated with PZ, and thus more highly correlated with prostate cancer, is consistent with the inventors' previous report of pPSA in the serum of PCa patients (10).

An assay which combines the ability to detect both TZ-associated BPSA and PZ-associated pPSA may therefore add significant specificity in the discrimination of BPH from PCa. In FIG. 5 we have plotted the ratio of BPSA/pPSA from our tissue samples. These plots show a clear discrimination of the TZ from PZ.

In accordance with the present invention, the forms of PSA in tissues differ from those reported in seminal plasma (7; 8). Table 1 shows that the majority of the PSA extracted from tissues contains minor levels of clips, while the BPSA is extensively clipped. The stratification of clips between the two forms of PSA further suggests that BPSA is a compartmentalized form of PSA derived from a more highly proteolytic environment.

PSA derived from pooled seminal plasma contained low levels of BPSA, ranging from 5–10%, while the major fraction of PSA eluting at 10 min by HIC-HPLC was about 30% clipped at Lys145 (data not shown). One of the earliest investigations to purify and characterize PSA from seminal plasma reported the presence of internal clips at residues Arg85, Lys148 and Lys185 (12). (In retrospect, it is believed that the sequence of this reference is off by three amino acids. Therefore, it appears that Lys148 should be Lys145, and Lys185 should be Lys182. ) Subsequent studies of inactive PSA have focused almost exclusively on the clip at Lys145, since this is the predominant clip and does in fact render PSA inactive.

Examination of the BPSA levels in the seminal plasma from individual donors may provide added insight into the variations of BPSA in prostate disease states. In accordance with the present invention, no pPSA in the inactive PSA may be detected from pooled seminal plasma, though individual cancer patients have not been tested.

The present invention also provides monoclonal antibodies specific for the BPSA and pPSA. If the serum free PSA levels reflect the population of PSA present in prostate tissue disease states, then an immunoassay which measures BPSA and pPSA may improve the discrimination of BPH from prostate cancer.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

DEPOSIT INFORMATION

A deposit of the monoclonal antibodies PS1Z134, PS1Z125, PS2C109, PS2C501, PS2C634, PS2C807, and PS2C837 disclosed above and recited in the appended claims has been made with the American Type Culture Collection (ATCC), 10801 University Boulevard, Manassas, Va. 20110.

The date of deposit was Apr. 11, 2002. The ATCC accession numbers have been assigned as follows:

PS2C807 has been assigned PTA-4223;

PS2C837 has been assigned PTA-4224;

PS2C634 has been assigned PTA-4225;

PS2C501 has been assigned PTA-4226;

PS2C109 has been assigned PTA-4227;

PS1Z134 has been assigned PTA-4228; and

PS1Z125 has been assigned PTA-4229.

The deposit will be maintained in the depository for a period of 30 years, or 5 years after the last request, or for the effective life of the patent, whichever is longer, and will be replaced as necessary during that period.

REFERENCE LIST

1. Catalona, W. J., Smith, D. S., Ratliff, T. L., Dodds, K. M., Coplen, D. E., Yuan, J. J., Tetros, J. A., and Andriole, G. L. Measurement of prostate-specific antigen in serum as a screening test for prostate cancer. N. Engl. J Med., 324: 1156–1161, 1991.

2. Oesterling, J. E. Prostate-specific antigen: a critical assessment of the most useful tumor marker for adenocarsoma of the prostate. J. Urol., 145: 907–923, 1991.

3. Labrie, F., Dupont, A., Suburu, R., Cusan, L., Tremblay, M., Gomez, J. L., and Emond, J. Serum prostate specific antigen as pre-screening test for prostate cancer [see comments]. J. Urol., 147: 846–851, 1992.

4. Stenman, U. H., Leinonen, J., Alfthan, H., Rannikko, S., Tuhkanen, K., and Alfthan, O: A complex between prostate specific antigen and $\alpha_1$-antichymotrypsin is the major form of prostate-specific antigen in serum of patients with prostatic cancer: assay of the complex improves clinical sensitivity for cancer. Cancer Res., 51: 222–226, 1991.

5. Catalona, W. J. Clinical utility of measurements of free and total prostate-specific antigen (PSA): A Review. Prostate, Supplement 7: 64–69, 1996.

6. Lilja, H., Christensson, A., Dahlen, U., Matikainen, M. T., Nilsson, O., Pettersson, K., and Lovgren, T. Prostate-Specific Antigen in Serum Occurs Predominantly in Complex with $\alpha_1$-antichymotrypsin. Clin. Chem., 37: 161814 1625, 1991.

7. Christensson, A., Laurell, C. B., and Lilja, H. Enzymatic activity of prostate-specific antigen and its reactions with extracellular serine proteinase inhibitors. Eur. J. Biochem., 194: 755–763, 1990.

8. Zhang, W. M., Leinonen, J., Kalkkinen, N., Dowell, B., and Stenman, U. H. Purification and characterization of different molecular forms of prostate-specific antigen in human seminal fluid. Clin. Chem., 41: 1567–1573, 1995.

9. Chen, Z., Chen, H., and Stamey, T. A. Prostate specific antigen in benign prostatic hyperplasia: purification and characterization. J. Urol., 157: 2166–2170, 1997.

10. Mikolajczyk, S. D., Grauer, L. S., Millar, L. S., Hill, T. M., Kumar, A., Rittenhouse, H. G., Wolfert, R. L., and Saedi, M. S. A precursor form of PSA (pPSA) is a component of the free PSA in prostate cancer serum. Urology, 50: 710–714, 1997.

11. Rittenhouse, H. G., Finlay, J. A., Mikolajczyk, S. D., and Partin, A. W. Human kallikrein 2 (hK2) and prostate-specific antigen (PSA): Two closely related, but distinct, kallikreins in the prostate. Crit. Rev. Clin. Lab. Sci., 35: 275–368, 1998.

12. Watt, K. W. K., Lee, P. J., MTimkulu, T., Chan, W. P., and Loor, R. Human prostate-specific antigen: Structural and functional similarity with serine proteases. Proc. Natl. Acad. Sci. USA, 83: 3166–3170, 1986.

13. Belanger, A., van Halbeek, H., Graves, H. C. B., Grandbois, K., Stamey, T., Huang, L. H., Poppe, I., and Labrie, F. Molecular mass and carbohydrate structure of porstate specific antigen: Studies for establishment of an international PSA standard. Prostate, 27: 187–197, 1995.

14. Rittenhouse, H. G., Finlay, J. A., Mikolajczyk, S. D., and Partin, A. W. Human kallikrein 2 (hK2) and prostate-specific antigen (PSA): Two closely related, but distinct, kallikreins in the prostate. Crit. Rev. Clin. Lab. Sci., 35: 275–368, 1998.

15. Kumar, A., Mikolajczyk, S. D., Groel, A. S., Millar, L. S., Saedi, M. S. Expression of Pro Form of Prostate-Specific Antigen by Mammalian Cells and Its Conversion to Mature, Active Form of Human Kallikrein 2. Cancer Res., 57, 3111–3114, 1997.

16. Knott, C. L., Kuss-Reichel, K., Liu, R. S., Wolfert, R. L. Development of Antibodies for Diagnostic Assays in: Principles and Practice of Immunoassay, Prince C. P., Newman D. J. (Eds.), Stockton Press, New York, 1977, pp. 37–64.

What is claimed is:

1. A method for distinguishing prostate cancer from benign prostatic hyperplasia (BPH) in a subject using different forms of prostate specific antigen (PSA) contained in a sample of the subject, comprising:
    (a) determining the amount of a first form of PSA contained in the sample;
    (b) determining the amount of a second form of PSA contained in the sample;
    (c) determining the ratio of the first form of PSA to the second form of PSA,
        wherein the first form of PSA is different from the second form of PSA, and wherein the first and second forms of PSA are selected from the group consisting of proPSA, total PSA and BPSA, wherein the BPSA in said method only comprises the form of PSA that comprises at least one clip at Lysine 182 of the amino acid sequence of a mature form of PSA; and (d) correlating the ratio of step (c) to the presence of prostate cancer or BPH in the subject.

2. A diagnostic method for determining the presence of BPH or prostate cancer in a subject, comprising the steps of:

(a) providing a first antibody that specifically binds to a first form of PSA;

(b) providing a second antibody that specifically binds to a second form of PSA;

(c) contacting the first antibody and the second antibody with a sample from the subject under a condition that allows the formation of a first binary complex comprising the first antibody and the first form of PSA and a second binary complex comprising the second antibody and the second form of PSA;

(d) detecting and determining the presence or amount of the first and second complexes;

(e) determining a ratio of the first complex to the second complex; and (f) relating the ratio of step (e) to the presence of BPH or prostate cancer in the subject, wherein the first and second forms of PSA are selected from the group consisting of proPSA, total PSA, and BPSA wherein the BPSA in said method only comprises the form of PSA that comprises at least one clip at Lysine 182 of the amino acid sequence of a mature form of PSA, and wherein the first form of PSA is different from the second form of PSA.

3. A kit for determining the presence of BPH or prostate cancer in a subject, comprising:

(a) a known amount of a first antibody which specifically binds to a first form of PSA; and (b) a known amount of a second antibody which specifically binds to a second form of PSA, wherein the first and the second antibodies, respectively, comprise a detectable label, and wherein the first form of PSA is BPSA wherein the BPSA in said kit only comprises the form of PSA that comprises at least one clip at Lysine 182 of the amino acid sequence of a mature form of PSA, and the second form of PSA is proPSA or PSA.

4. The method of claim 1, wherein the ratio of step (c) is a ratio of proPSA to BPSA or inversely thereof.

5. The method of claim 1, wherein the proPSA is selected from a group consisting of [−1]pPSA, [−2]pPSA, [−4]pPSA, [−5]pPSA and [−7]pPSA, or any combination thereof.

6. The method of claim 5, wherein the proPSA is [−2]pPSA or [−4]pPSA.

7. The method of claim 1, wherein the BPSA comprises one clip at Lys182 of the amino acid sequence of a mature form of PSA, and one or more additional clips at a location selected from a group consisting of Ile1, Lys145 and Lys146.

8. The method of claim 1, wherein the sample is a mammalian tissue sample.

9. The method of claim 1, wherein the sample is a sample of human physiological fluid.

10. The method of claim 9,wherein the human physiological fluid is serum, seminal plasma, urine or plasma.

11. The method of claim 1, wherein step (a) further comprises the steps of:

(a) contacting an amount of an antibody which specifically binds to the proPSA with the sample under a condition that allows the formation of a binary complex comprising the antibody and the proPSA; and (b) detecting or determining the presence or amount of the complex.

12. The method of claim 11, wherein the antibody comprises a polyclonal antibody or a monoclonal antibody.

13. The method of claim 11, wherein the antibody comprises a monoclonal antibody selected from a group consisting of PS1Z134 and PS1Z125.

14. The method of claim 12, wherein in step (b) of claim 11 the antibody comprises a detectable label or binds to a detectable label to form a detectable ternary complex.

15. The method of claim 1, wherein step (b) further comprises the steps of:

(a) contacting an amount of an antibody which specifically binds to BPSA with the sample under a condition that allows the formation of a binary complex comprising the agent and the BPSA; and (b) detecting or determining the presence or amount of the complex.

16. The method of claim 15, wherein the antibody comprises a polyclonal antibody or a monoclonal antibody.

17. The method of claim 16, wherein the antibody comprises a monoclonal antibody selected from a group consisting of PS2C109, PS2C501, PS2C634, PS2C807 and PS2C837.

18. The method of claim 16, wherein in step (b) of claim 15 the antibody comprises a detectable label or binds to a detectable label to form a detectable ternary complex.

19. The diagnostic method of claim 2, wherein the ratio of step (e) is a ratio of proPSA to BPSA or inversely thereof.

20. The diagnostic method of claim 2, wherein the first form of PSA is proPSA, and the second form of PSA is BPSA, and wherein step (c) comprises the steps of:

(a) contacting the first antibody with the sample under a condition that allows the formation of a first binary complex comprising the first antibody and the proPSA; and (b) contacting the second antibody with the sample under a condition that allows the formation of a second binary complex comprising the second antibody and the BPSA.

21. The diagnostic method of claim 2, wherein the first and the second antibodies, respectively, comprise a detectable label or bind to a detectable label to form a respective detectable ternary complex.

22. The diagnostic method of claim 21, wherein the first and the second antibodies, respectively, comprise different detectable labels or bind to a different detectable label to form a respective detectable ternary complex.

23. The diagnostic method of claim 2, wherein the sample is a mammalian tissue sample.

24. The diagnostic method of claim 2, wherein the sample is a sample of human physiological fluid.

25. The diagnostic method of claim 24; wherein the human physiological fluid is serum, seminal plasma, urine or plasma.

26. The diagnostic method of claim 2, wherein the first antibody comprises a polyclonal antibody or a monoclonal antibody.

27. The diagnostic method of claim 26, wherein the first antibody is a monoclonal antibody selected from a group consisting of PS1Z134 and PS1Z125.

28. The diagnostic method of claims 2, wherein the second antibody is a polyclonal antibody or a monoclonal antibody.

29. The diagnostic method of claim 28, wherein the second antibody is a monoclonal antibody selected from a group consisting of PS2C109, PS2C501, PS2C634, PS2C807 and PS2C837.

30. The diagnostic method of claim 20, wherein the proPSA is selected from a group consisting. of [−2], [−4], [−5] and [−7]proPSA.

31. The diagnostic method of claim 20, wherein the BPSA comprises one clip at Lys182 and one or more clips at a location selected from a group consisting of Ile1, Lys145 and Lys146.

32. The kit of claim 3, wherein the first and the second antibodies, respectively, comprise a different detectable label or bind to a different detectable label to form a respective detectable ternary complex.

33. The kit of claim 3, wherein the first antibody comprises a polyclonal antibody or a monoclonal antibody.

34. The kit of claim 33, wherein the first antibody is a monoclonal antibody selected from a group consisting of PSM773, PS1Z134 and PS1Z125.

35. The kit of claim 3, wherein the second antibody is a polyclonal antibody or a monclonal antibody.

36. The kit of claim 35, wherein the second antibody is a monoclonal antibody selected from a group consisting of PS2C109, PS2C501, PS2C634, PS2C807 and PS2C837.

37. The kit of claim 3, wherein the first form of PSA is proPSA selected from a group consisting of [−2], [−4], [−5] and [−7]proPSA.

38. The kit of claim 3, wherein the second form of PSA is BPSA comprising one clip at Lys182 and one or more clips at a location selected from a group consisting of Ile1, Lys145 and Lys146.

* * * * *

UNITED STATES PATENT AND TRADEMARK OFFICE
CERTIFICATE OF CORRECTION

PATENT NO. : 6,423,503 B1
APPLICATION NO. : 09/303339
DATED : July 23, 2002
INVENTOR(S) : Stephen D. Mikolajczyk et al.

It is certified that error appears in the above-identified patent and that said Letters Patent is hereby corrected as shown below:

In column 14, line 38 change "MIC-HPLC" to --HIC-HPLC--.

Signed and Sealed this

Fifth Day of December, 2006

JON W. DUDAS
*Director of the United States Patent and Trademark Office*